United States Patent [19]
Kotani et al.

[11] Patent Number: 5,912,261
[45] Date of Patent: Jun. 15, 1999

[54] CARBOXYALKYL HETEROCYCLIC DERIVATIVES

[75] Inventors: Takayuki Kotani; Kaoru Okamoto; Yasuhiro Nagaki, all of Hyogo, Japan

[73] Assignee: Nippon Zoki Pharmaceutical Co., Ltd., Osaka, Japan

[21] Appl. No.: 08/575,023

[22] Filed: Dec. 19, 1995

[30] Foreign Application Priority Data

Dec. 20, 1994 [JP] Japan ................................ 6-335821

[51] Int. Cl.⁶ ................ C07D 233/66; C07D 239/02; C07D 233/74; A61K 31/415
[52] U.S. Cl. ................ 514/400; 514/386; 514/389; 514/392; 514/275; 514/396; 514/402; 514/269; 544/300; 544/302; 544/309; 544/311; 544/314; 544/319; 548/317.5; 548/319.5; 548/319.1
[58] Field of Search ................ 514/386, 389, 514/392, 269, 278, 400; 544/300, 302, 314, 309, 319; 548/317.5, 319.5

[56] References Cited

U.S. PATENT DOCUMENTS

| Re. 32,919 | 5/1989 | Sarnoff ............................. 514/2 |
| 3,818,031 | 6/1974 | Baerlocher et al. ............. 260/309.5 |
| 4,096,130 | 6/1978 | Kraft et al. ...................... 260/775 |
| 4,647,574 | 3/1987 | Ienaga et al. .................... 514/390 |
| 4,656,034 | 4/1987 | Sarnoff ............................. 424/94 |
| 4,661,469 | 4/1987 | Sarnoff ............................. 514/2 |
| 4,683,240 | 7/1987 | Ienaga et al. .................... 514/390 |
| 4,772,585 | 9/1988 | Sarnoff et al. ................... 514/2 |
| 4,985,453 | 1/1991 | Ishii et al. ........................ 514/386 |
| 5,002,930 | 3/1991 | Sarnoff et al. ................... 514/2 |
| 5,084,473 | 1/1992 | Mikami et al. .................... 514/390 |

FOREIGN PATENT DOCUMENTS

| 0 160 618 A1 | 11/1985 | European Pat. Off. . |
| 0 194 226 A1 | 9/1986 | European Pat. Off. . |
| 0 353 198 A1 | 1/1990 | European Pat. Off. . |
| 0 412 940 A2 | 2/1991 | European Pat. Off. . |
| 0721 944 | 7/1996 | European Pat. Off. . |
| 26 12 926 A1 | 10/1977 | Germany . |
| 63-166870 | 7/1988 | Japan . |
| 2-40368 | 2/1990 | Japan . |
| 2225485 | 9/1990 | Japan . |
| 563 711 | 7/1975 | Switzerland . |
| 2 214 448 | 10/1972 | United Kingdom . |
| WO 86/01110 | 2/1986 | WIPO . |
| WO 89/02890 | 4/1989 | WIPO . |

OTHER PUBLICATIONS

Grangier et al., (CAS online print out of CA 122:187438, abstract of J. Hetrocyclic Chem. (1994), 31 (6), 1707–14.
Malamas et al., CAS online print out of CA 114:247224, abstract of J. Med. Chem. (1991), 34(4), 1492–503.
Brownlee, et al., "Aminoguanidine Prevents Diabetes–Induced Arterial Wall Protein Cross–Linking", *Science*, vol. 232, 1986, pp. 1629–1632.

Ishii, et al., "Highly Selective Aldose Reductase Inhibitors", *J. Med Chem.*, vol. 39, No. 9, 1996, pp. 1924–1927.
Kotani, et al., "Highly Selective Aldose Reductase Inhibitors. 3." *J. Med Chem.*, vol. 40, No. 5, 1997, pp. 684–694.
Kotani, et al., Highly Selective Aldose Redfuctase Inhibitors. II, *Chem. Pharm. Bull.*, vol. 45, No. 2, 1997, pp. 297–304.
Malamas et al. (J. Med. Chem. (1991), vol. 34, pp. 1492–1503).
Grangier et al. (J. Heterocyclic Chem., 31, 1707, 1994).
CA 60:532c, (Mitsubishi Chemical Industries Co. Ltd., (by Masatsune Sato). ('63), Japan, 15, 392).
K. Ogawva, et al., "Syntheses of substituted 2,4–dioxo–thienopyrimidin–1–acetic acids and their evaluation as aldose reductase inhibitors", *European Journal of Medicinal Chemistrychimica Therapeutica*, vol. 28, No. 10, 1993, pp. 769–781.
Kanazu, et al., "Aldehyde reductase is a major protein associated with 3–deoxyglucosone reductase activity in rat, pig and human livers", *Biochem J.*, 279, 903–906 (1991).
Flynn, "Aldehyde Reductases: Monomeric Nadph–Dependent Oxidoreductases With Multifunctional Potential", *Biochem. Pharmacol.*, vol. 31, No. 17, 2705–2712 (1982).
Patton, *J. Org. Chem.*, 32, No. 2, pp. 383–388 (1967).
Krasnov et al., (CA 119:8771, abstract of Zh. Org. Khim. (1992), 28(7), 1531–7.
Ishii et al. (CA 119:180804, abstract of JP 05043555) 1993.
Henmi et al. (CA 113:23919 abstract of JP 02019363) 1990.

*Primary Examiner*—Jose' G. Dees
*Assistant Examiner*—Sabiha N. Qazi
*Attorney, Agent, or Firm*—Fisher, Christen & Sabol

[57] ABSTRACT

Carboxyalkyl heterocyclic derivatives, pharmaceutically acceptable salts thereof, and therapeutic agents containing said compounds as an effective component are useful pharmaceuticals for the treatment of diabetic complications such as diabetic neuropathy, diabetic cataracts and retinopathy, diabetic nephropathy, diabetic dermopathy, and other diabetic microangiopathy. The compounds of the present invention are represented by the following general formula (A):

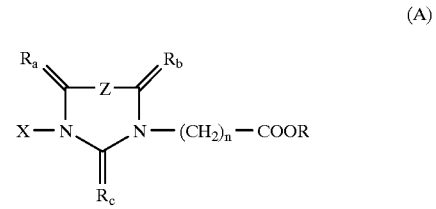

(A)

The compounds of the present invention exhibit excellent inhibitory action towards aldose reductase with a high enzyme selectivity. Accordingly, they are useful as drugs for the therapy and prevention of various types of diabetic complications without substantially inhibiting aldehyde reductase.

17 Claims, No Drawings

CARBOXYALKYL HETEROCYCLIC DERIVATIVES

FIELD OF THE INVENTION

The present invention relates to novel carboxyalkyl heterocyclic derivatives and pharmaceutically acceptable salts thereof and also to pharmaceutical compositions containing said compounds as the effective component.

BACKGROUND OF THE INVENTION

Diabetic neuropathy, diabetic cataracts and retinopathy, diabetic nephropathy, diabetic dermopathy and other diabetic microangiopathy have been known as chronic, difficult to treat diseases resulting from diabetes. Participation of a polyol metabolic system may be a cause of those diabetic complications.

Thus, when a hyperglycemic state results from diabetes, utilization of glucose via a polyol metabolic pathway increases several-fold compared with the normal state. Also, production of sorbitol by an aldose reductase is accelerated. It is presumed that, as a result thereof, intracellular sorbitol in peripheral nerves, retina, kidney, lens, artery and the like accumulates excessively. The excessive sorbitol accumulation leads to cell edema and hypofunction due to an abnormal osmotic pressure in the cells.

Accordingly, agents for inhibiting aldose reductase have been thought to be effective for the therapy and the prevention of diabetic complications and have been studied. However, conventional aldose reductase inhibitors are problematic because they strongly inhibit other enzymes which do not participate in the polyol metabolic pathway. For example, an aldehyde reductase may be undesirably inhibited by conventional aldose reductase inhibitors.

Under such circumstances, the present inventors have conducted a study to obtain inhibitors having a high enzyme selectivity toward aldose reductase which participates in the production of sorbitol with an object of providing therapy for and prevention of the above-mentioned diabetic complications. As a result, the present inventors have found that the carboxyalkyl heterocyclic derivatives of the present invention exhibit an excellent inhibitory action with a high enzyme selectivity to aldose reductase whereby the present invention has been achieved.

SUMMARY OF THE INVENTION

The carboxyalkyl heterocyclic derivatives and their pharmaceutically acceptable salts of the present invention exhibit unexpectedly superior selective inhibition of aldose reductase. The derivatives and their salts substantially inhibit aldose reductase and the production of intracellular sorbitol without substantial inhibition of other enzymes, such as aldehyde reductase which do not participate in the polyol metabolic pathway.

The compounds of the present invention include carboxyalkyl heterocyclic derivatives represented by the general formula (A) or pharmaceutically acceptable salts of the derivatives represented by the general formula (A):

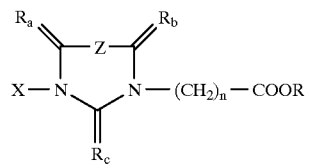

(A)

wherein two of the substituents $R_a$, $R_b$ and $R_c$ are oxygen while the remaining substituent is sulfur, lower alkylene, unsubstituted or a combination of hydrogen and hydroxyl, X is
  benzyl which may be substituted with nitro and/or substituted with halogen,
  benzothiazolylmethyl which may be substituted with nitro and/or substituted with halogen, or
  naphthylmethyl which may be substituted with nitro and/or substituted with halogen;

R is hydrogen or lower alkyl;

n is an integer of 1 to 3; and

Z indicates a direct bond or a bond consisting of one carbon atom.

The compounds of the present invention include dioxoimidazolidine derivatives and their pharmaceutically acceptable salts when Z is a direct bond between the carbon atoms to which the $R_a$ and $R_b$ substituents are attached. When Z is a bond consisting of one carbon atom between the carbon atoms to which the $R_a$ and $R_b$ substituents are attached, the compounds of the present invention are dioxopyrimidine derivatives and pharmaceutically acceptable salts thereof. The present invention also provides pharmaceutical compositions containing at least one of the derivatives of formula (A) or at least one salt thereof in a pharmaceutically acceptable amount.

The compounds and pharmaceutical compositions of the present invention may be used in pharmaceutically effective amounts to treat and prevent various types of diabetic complications such as diabetic neuropathy, diabetic cataracts and retinopathy, diabetic nephropathy, diabetic dermopathy and other diabetic microangiopathy.

DETAILED DESCRIPTION OF THE INVENTION

The present invention provides novel carboxyalkyl heterocyclic derivatives and pharmaceutically acceptable salts thereof having an excellent inhibitory action towards aldose reductase. The carboxyalkyl heterocyclic derivatives and their salts exhibit a high enzyme selectivity for aldose reductase thereby avoiding problems associated with the inhibition of other enzymes which do not participate in the polyol metabolic pathway. The derivatives and their pharmaceutically acceptable salts may be used in pharmaceutically effective amounts in therapeutic agents or pharmaceutical compositions for the treatment of diabetic complications.

The carboxyalkyl heterocyclic.derivatives in accordance with the present invention are represented by the following formula (A):

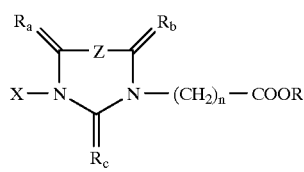

(A)

wherein any two of $R_a$, $R_b$ and $R_c$ are oxygen while the third or remaining group or substituent is sulfur, lower alkylene, unsubstituted (i.e. only hydrogen is bonded to the ring at the position of the third group), or a combination of hydrogen and hydroxyl (i.e. one hydrogen and one hydroxyl are each bonded to the ring at the position of the third group); X is benzyl which may be substituted with nitro and/or substituted with halogen, benzothiazolylmethyl which may be substituted with nitro and/or substituted with halogen, or naphthylmethyl which may be substituted with nitro and/or substituted with halogen; R is hydrogen or lower alkyl; n is an integer of 1 to 3; and Z indicates a direct bond (in which case the heterocyclic ring is 5-membered) or a bond consisting of one carbon atom (in which case the heterocyclic ring is 6-membered).

The compounds of the present invention include dioxoimidazolidine derivatives represented by the following general formula (I) and dioxopyrimidine derivatives represented by the following general formula (II) and pharmaceutically acceptable salts of the derivatives of formulas I and II:

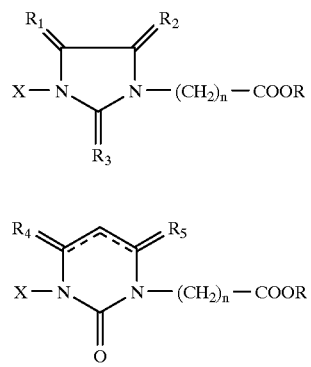

In the above-given general formula (I), any two of $R_1$, $R_2$ and $R_3$ are oxygen while the third or remaining group or substituent is sulfur, lower alkylene (preferably an alkylene having 1 to 3 carbon atoms such as methylene, ethylene and propylene; most preferably, methylene), unsubstituted (i.e., two hydrogens are each bonded to the ring at the position of the third group), or a combination of hydrogen and hydroxyl (i.e., each of hydrogen and hydroxyl are bonded to the ring at the position of the third group). In the general formula (II), one of $R_4$ and $R_5$ is oxygen while the other is unsubstituted (i.e., only one hydrogen is bonded to the ring).

In the general formulae (I) and (II), X is benzyl which may be substituted with nitro and/or substituted with halogen such as fluorine, chlorine, bromine and iodine, benzothiazolylmethyl which may be substituted with nitro and/or substituted with halogen such as fluorine, chlorine, bromine and iodine, or naphthylmethyl which may be substituted with nitro and/or substituted with halogen such as fluorine, chlorine, bromine and iodine; R is hydrogen or lower alkyl (preferably, an alkyl having 1–3 carbon atoms such as methyl, ethyl, propyl, isopropyl, butyl, isobutyl, sec-butyl and tert-butyl); and n is an integer of 1–3 (preferably 1). The two broken lines in the general formula (II) represents one single bond and one double bond in the linkage between $R_4$ and $R_5$ with the single bond being on the same side of the linkage as the oxygen substituent represented by $R_4$ or $R_5$ while the other side of the linkage between $R_4$ and $R_5$ is a double bond. For example, if $R_4$ is oxygen, then $R_5$ is hydrogen and the compounds of formula II are:

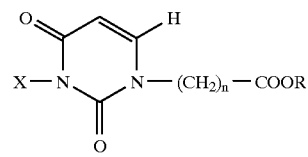

wherein X, R, and n are defined as above.

The carboxyalkyl heterocyclic derivatives of the present invention include the pharmaceutically acceptable salts of the compounds represented by the above-given general formulae. Exemplary salts are salts of the compounds of general formulae A, I, and II with an alkali metal such as sodium and potassium, with an alkali earth metal such as calcium and magnesium, with a metal such as aluminum, and with a base such as ammonia and organic amines.

The pharmaceutically acceptable salts may be manufactured by conventional methods starting from the carboxyalkyl heterocyclic derivatives of the present invention in the free state or by conversion from one salt to another salt.

When there are stereoisomers such as cis-trans isomers, optical isomers and conformational isomers for the compounds of the present invention, or when the compounds exist as hydrates, the present invention includes any and all of such stereoisomers and hydrates.

The carboxyalkyl heterocyclic derivatives of the present invention may be manufactured, for example, by the following methods:

(1) In the case of dioxoimidazolidine derivatives in which $R_3$ in the general formula (I) is methylene, oxamic acid having a group corresponding to a substituent X is first made to react with glycine which is esterified, for example, with a trimethylsilyl group to give an ester of X-substituted oxamideacetate. This ester is heated to reflux in acetic anhydride with sodium acetate or the like to give an ester of 3-X-2-methylidene-4,5-dioxoimidazolidine-1-carboxylic acid. Then the ester, such as the trimethylsilyl ester, is hydrolyzed to give a compound of the present invention in which R is hydrogen.

(2) In the case of dioxoimidazolidine derivatives in which $R_3$ in the general formula (I) is sulfur, thiourea having a group corresponding to a substituent X and an esterified carboxyalkyl group are made to react with oxalyl chloride whereupon an ester of 3-X-4,5-dioxo-1-thioxoimidazolidine-1-carboxylic acid of the present invention is manufactured. When this ester compound is hydrolyzed in conventional manner, the compound of the present invention in which R is hydrogen is obtained.

(3) In the case of dioxoimidazolidine derivatives in which $R_1$ in the general formula (I) is unsubstituted, an amino acetate having a group corresponding to a substituent X is first made to react with an alkyl isocyanatoacetate to give X-substituted N,N'-bis(alkoxycarbonylalkyl)urea. The latter is then heated to reflux in a mixed solvent of acetic acid and concentrated hydrochloric acid to produce 1-X-2,4-dioxoimidazolidine-3-carboxylic acid.

(4) In the case of dioxoimidazolidine derivatives in which $R_2$ in the general formula (I) is unsubstituted, alkyl 2,4-dioxoimidazolidine-1-carboxylate is made to react with a substituent X compound which is bonded with halogen, hydroxyl, lower alkyl—$SO_2$—O—or phenyl—$SO_2$—O— which may be substituted with lower alkyl whereby the substituent X is introduced into a dioxoimidazolidine skeleton to give an ester of the present invention. When this ester is subjected to a conventional hydrolysis as that mentioned hereinabove, a compound of the present invention in which R is hydrogen is obtained.

(5) In the case of dioxoimidazolidine derivatives in which $R_1$ in the general formula (I) is methylene, alkyl isocyanatocarboxylate is made to react with methyl 2-(X-substituted amino)-3-hydroxypropionate followed by treatment with an alkali such as potassium hydroxide or sodium hydroxide in a solvent such as water or alcohol to produce 1-X-5-methylidene-2,4-dioxoimida-zolidine-3-carboxylic acid.

(6) In the case of dioxoimidazolidine derivatives in which $R_2$ in the general formula (I) is methylene, 3-X-substituted 5-benzylthioxymethylimidazolidine-2,4-dione is treated with sodium hydride and then made to react with alkyl halocarboxylate to give alkyl 3-X-5-methylidene-2,4-dioxoimidazolidine-1-carboxylate. When this ester is subjected to a conventional hydrolysis as mentioned hereinabove, a compound of the present invention in which R is hydrogen is produced.

(7) In the case of dioxoimidazolidine derivatives in which $R_1$ in the general formula (I) is hydrogen and hydroxyl, N-X-substituted urea is first made to react with benzyl 2-benzyloxy-2-hydroxyacetate to give 5-hydroxy-1-X-2,4-dioxoimidazolidine. Then this is made to react with alkyl halocarboxylate to manufacture alkyl 5-hydroxy-1-X-2,4-dioxoimidazolidine-3-carboxylate. This ester can be converted to the compound of the present invention in which R is hydrogen when subjected to a conventional hydrolysis in the same manner as described above.

(8) In the case of dioxoimidazolidine derivatives in which $R_2$ in the general formula (I) is hydrogen and hydroxyl, alkyl N-carbamoylaminocarboxylate is made to react with benzyl 2-benzyloxy-2-hydroxyacetate to give alkyl 5-hydroxy-2,4-dioxoimidazolidine-1-carboxylate. The latter compound is then reacted with a substituent X compound which is bonded with halogen, hydroxyl, lower alkyl—$SO_2$—O— or phenyl—$SO_2$—O— which may be substituted with lower alkyl to introduce a substituent X into the dioxoimidazolidine skeleton whereupon an ester of the present invention is obtained. When this ester is subjected to the same conventional hydrolysis as mentioned above, the compound of the present invention in which R is hydrogen is obtained.

(9) In the case of dioxopyrimidine derivatives in which $R_5$ in the general formula (II) is unsubstituted, alkyl 2,4-dioxo-1,2,3,4-tetrahydropyrimidine-1-carboxylate is treated with sodium hydride and then reacted with a substituent X compound which is bonded with halogen, hydroxyl, lower alkyl—$SO_2$—O— or phenyl—$SO_2$—O— which may be substituted with lower alkyl to introduce a substituent X into the dioxopyrimidine skeleton whereupon alkyl 3-X-2,4-dioxo-1,2,3,4-tetrahydropyrimidine-1-carboxylate is obtained. This ester can be converted to a compound of the present invention in which R is hydrogen by a conventional hydrolysis.

(10) In the case of a dioxopyrimidine derivatives in which $R_4$ in the general formula (II) is unsubstituted, 3-X-uracil is treated with sodium hydride and then caused to react with alkyl halocarboxylate to give 1-X-2,4-dioxo-1,2,3,4-tetrahydropyrimidine-3-carboxylate. When this ester is subjected to the same conventional hydrolysis as above, the compound of the present invention in which R is hydrogen is manufactured.

The resulting compounds of the present invention may be purified by common means such as distillation, chromatography and recrystallization and identified by means of, for example, elementary analysis, melting point measurement, infrared (IR), nuclear magnetic resonance (NMR), and mass spectroscopy (MS) analysis.

The present invention is illustrated by the following examples wherein all parts, percentages, and ratios are by weight, all temperatures are in °C., and all reactions are conducted at about atmospheric pressure unless indicated to the contrary.

EXAMPLE 1

(1) A reaction mixture solution comprising 150 mL of methylene chloride solution containing 6.96 g of N-(3-nitrobenzyl)-oxamic acid, 6.8 g of 2-(trimethyl)silyl ethyl ester of glycine and 0.1 g of 4-N,N'-dimethylaminopyridine was treated with 8.62 g of a water-soluble carbodiimide hydrochloride at 0° C. After the above mixture was stirred at room temperature for 20 hours, it was poured over water and extracted with methylene chloride several times. The extracts were combined, washed with a saturated saline solution, dried over sodium sulfate and concentrated. The concentrate was purified by a silica gel column and recrystallized from a mixed solvent of ethyl acetate and acetone to give 4.41 g of N-2-(trimethylsilyl)ethyl N'-(3-nitrobenzyl) oxamideacetate.

(2) The above-prepared oxamideacetate product (4.90 g) from several production runs and 3.35 g of sodium acetate were heated to reflux for two days in acetic anhydride. The reaction mixture was neutralized with sodium bicarbonate and extracted with ethyl acetate thrice. The extracts were combined, washed with a saturated solution of sodium bicarbonate and with a saturated saline solution, dried over sodium sulfate and concentrated in vacuo. The resulting residue was purified by a silica gel column and recrystallized from a mixed solvent of ethyl acetate and acetone to give 2.19 g of 2-(trimethylsilyl)-ethyl 3-(3-nitrobenzyl)-2-methylidene-4,5-dioxoimidazolidine-1-acetate.

(3) The above-prepared dioxoimidazolidine product (0.76 g) of paragraph (2) was dissolved in a mixed solvent of 20 mL of tetrahydrofuran and 10 mL of hexane, then a 1M solution of tetrabutylammonium fluoride in tetrahydrofuran was added thereto at room temperature and the mixture was vigorously stirred for 2.5 hours. The reaction mixture was acidified with 2N hydrochloric acid and extracted with ethyl acetate thrice. The combined extract was dried over sodium sulfate and concentrated, followed by recrystallization from ethanol to give 3-(3-nitrobenzyl)-2-methylidene-4,5-dioxoimidazolidine-1-acetic acid [Compound 1]. The melting point, MS, IR, NMR, and elementary analysis for the compound were:

Melting point: 160.0–160.5° C.; MS(EI,70eV): 305($M^+$, 30), 288(32), 176(30), 136(100), 100(45), 90(91), 89(65), 54(56); IR(KBr): 3020(OH), 1740(C=O), 1684(C=O), 1533($NO_2$), 1437, 1348($NO_2$), 1192 $cm^{-1}$; $^1$H-NMR (DMSO-$d_6$): 4.10(s,2H,N—$CH_2$—CO), 4.47(s,1H,$CH_2$=), 4.52(s,1H,$CH_2$=), 4.70(d,J=16.2 Hz,1H,$CH_2$—Ar), 4.80(d, J=16.2 Hz,1H,$CH_2$—Ar), 7.65(dd,J=12.3,8.4 Hz,1H,Ar), 7.83(d,J=12.3 Hz,1H,Ar), 8.16(d,J=8.4 Hz,1H,Ar), 8.24(s, 1H,Ar), 12.96(brs,1H,OH);

Elementary analysis ($C_{13}H_{11}N_3O_6$ 0.9$H_2O$): Calculated; (C=48.57,H=4.01,N=13.07), Found (C=48.84,H=3.92,N=12.77)

EXAMPLE 2

(1) To 3.0 g of N-(ethoxycarbonylmethyl)-N'-(3-nitrobenzyl)-urea was added 5.0 g of a lawson reagent dissolved in 30 mL of 1,4-dioxane and the mixture was heated to reflux for 1.5 hours. The reaction mixture was extracted with ethyl acetate several times and the extracts were combined, washed with a saturated saline solution, dried over sodium sulfate and concentrated. The resulting residue was purified by a silica gel column to give 2.5 g of N-(ethoxycarbonylmethyl)-N'-(3-nitrobenzyl)thiourea.

(2) The above-prepared thiourea product (2.5 g) was dissolved in 10 mL of methylene chloride and the solution was dropped into 10 mL of methylene chloride containing 1.0 mL of oxalyl chloride at room temperature. The reaction mixture was stirred at room temperature for eight hours and concentrated in vacuo. This was then purified by a silica gel column to give ethyl 3-(3-nitrobenzyl)-4,5-dioxo-2-thioxoimidazolidine-1-acetate.

(3) The above-prepared thioxoimidazolidine-1-acetate product of paragraph (2) was heated to reflux in a mixed solvent of 4.5 mL of acetic acid and 1.5 mL of hydrochloric acid for one hour and concentrated. To the resulting residue were added 4.5 mL of acetic acid and 1.5 mL of hydrochloric acid and the mixture was heated to reflux for one hour. After concentration, the residue was recrystallized from a mixed solvent of ethanol and hexane to give 0.23 g of 3-(3-nitrobenzyl)-4,5-dioxo-2-thioxoimidazolidine-1-acetic acid [Compound 2]. The melting point, MS, IR, NMR, and elementary analysis for the compound were:

Melting point: 188.0–188.5° C.; MS(EI,70eV): 323($M^+$, 67), 177(55), 161(63), 136(90), 90(100); IR(KBr): 3000 (OH), 1784(C=O), 1722(C=O), 1531($NO_2$), 1435(C=S), 1346($NO_2$), 1113 $cm^{-1}$; $^1$H-NMR(DMSO-$d_6$): 4.56(s,2H, N—$CH_2$—CO), 5.20(s,2H,$CH_2$—Ar), 7.65(dd,J=8.0,7.3 Hz,1H,Ar), 7.83(d,J=7.7 Hz,1H,Ar), 8.16(d,J=8.0 Hz,1H, Ar), 8.26(s,1H,Ar), 13.38(brs,1H,OH); Elementary analysis ($C_{12}H_9N_3O_6S$): Calculated; (C=44.58,H=2.81,N=13.00), Found (C=44.55,H=2.98,N=12.79)

EXAMPLE 3

(1) A solution (50 mL) of ether in which 5.3 g of N-benzyl aminoacetate was dissolved was added to 50 mL of solution of ether containing 3.4 mL of ethyl isocyanate acetate at room temperature and the mixture was vigorously stirred for 14 hours. The reaction mixture was concentrated and the residue was purified by a silica gel column to give 5.5 g of N-benzyl-N,N'-bis(ethoxycarbonylmethyl)urea having a melting point of 64.0–65.0° C.

(2) A mixture of 1.7 g of the above-prepared urea product of paragraph (1) dissolved in 3 mL of acetic acid and 1 mL of concentrated hydrochloric acid was heated to reflux for four hours. After evaporating the solvent therefrom, 3 mL of acetic acid and 1 mL of concentrated hydrochloric acid were added to the residue followed by stirring for two hours. The resulting component was concentrated, washed well with water and recrystallized from ethanol to give 1.2 g of 1-benzyl-2,4-dioxoimidazolidine-3-acetic acid [Compound 3]. The melting point, MS, IR, NMR, and elementary analysis for the compound were:

Melting point: 139.5–141.0° C.; MS(EI,70eV): 248($M^+$, 27), 202(24), 189(11), 132(34), 118(39), 91(100), 65(32); IR(KBr): 2940(OH), 1759(C=O), 1749(C=O), 1684 (C=O), 1470, 1207, 752, 702 $cm^{-1}$; $^1$H-NMR($CDCl_3$): 3.99(s,2H,N—$CH_2$—CO), 4.11(s,2H,N—$CH_2$—CO), 4.53 (s,2H,$CH_2$—Ar), 7.20–7.40(m,5H,Ar), 13.15(brs,1H,OH);

Elementary analysis ($C_{12}H_{12}N_2O_4$): Calculated; (C=58.06,H=4.87,N=11.28), Found (C=57.54,H=5.00,N=11.02)

(3) The same operations as performed above in paragraphs (1) and (2) were carried out using N-3-nitrobenzyl aminoacetate as a starting material to give 1-(3-nitrobenzyl)-2,4-dioxoimidazolidine-3-acetic acid [Compound 4]. The melting point, MS, IR, NMR, and elementary analysis for the compound were:

Melting point: 168.0–170.0° C.; MS(EI,70eV): 293($M^+$, 6), 276(85), 246(20), 163(24), 147(31), 136(97), 90(100), 56(55), 42(88); IR(KBr): 3100(OH), 1774(C=O), 1745 (C=O), 1714(C=O), 1533($NO_2$), 1469, 1359($NO_2$), 1238, 1151, 752, 700 $cm^{-1}$; $^1$H-NMR(DMSO-$d_6$): 4.08(s,2H,N—$CH_2$—CO), 4.12(s,2H,N—$CH_2$—$CO_2$), 4.68(s,2H,$CH_2$—Ar), 7.67(dd,J=8.6,7.7 Hz,1H,Ar), 7.76(d,J=7.7 Hz,1H,Ar), 8.16(s,1H,Ar), 8.17(d,J=8.6 Hz,1H,Ar), 13.20(brs,1H,OH);

Elementary analysis ($C_{12}H_{11}N_3O_6$): Calculated; (C=49.15,H=3.78,N=14.33), Found (C=49.02,H=3.84,N=14.13)

EXAMPLE 4

(1) Concentrated hydrochloric acid (24.0 mL) was gradually dropped into 350 mL of an aqueous solution containing 27.5 g of diethyl iminodiacetate and 23.3 g of potassium cyanate. After stirring at room temperature for 18 hours, the reaction mixture was concentrated in vacuo. The residue was extracted with ethyl acetate several times and the extracts were combined followed by drying over sodium sulfate. The dried extract was concentrated and the residue was recrystallized from ethanol to give 11.1 g of ethyl 2,4-dioxoimidazolidine-1-acetate as white crystals.

(2) A solution of 815 mg of the above-prepared dioxoimidazolidine-l-acetate product of paragraph (1) dissolved in 30 mL of dimethylformamide was dropped into a suspension of 221 mg of sodium hydride in 20 mL of dimethylformamide at not higher than 0° C. The mixture was stirred for one hour more at the same temperature condition and then a solution of 1.3 g of 3-nitrobenzyl bromide dissolved in 30 mL of dimethylformamide was dropped thereinto at 0° C. The reaction mixture was stirred for two hours and added to an ice-cooled 2N hydrochloric acid with vigorous stirring. The resulting reaction mixture was extracted with ethyl acetate several times and the combined extract was washed with a saturated physiological saline solution and concentrated to give a residue. This residue was purified by a silica gel column to give 1.32 g of ethyl 3-(3-nitrobenzyl)-2,4-dioxoimidazolidine-1-acetate.

(3) The above-prepared dioxoimidazolidine-1-acetate product of paragraph (2) from several production runs (1.7 g) was heated to reflux in a mixed solvent of 12 mL of acetic acid and 4 mL of concentrated hydrochloric acid for one hour. After evaporating the solvent therefrom, 12 mL of acetic acid and 4 mL of concentrated hydrochloric acid were added to the residue and the mixture was heated to reflux for one hour more. The refluxed mixture was poured over a mixed solution of ethyl acetate and 10% sodium hydroxide, the mixture was extracted with 10% sodium hydroxide several times and the resulting aqueous extract was subjected to a reverse extraction several times. The extracts were combined, dried over sodium sulfate, concentrated and recrystallized from ethanol to give 350 mg of 3-(3-nitrobenzyl)-2,4-dioxoimidazolidine-1-acetic acid [Compound 6]. The melting point, MS, IR, NMR, and elementary analysis for the compound were:

Melting point: 165.0–166.0° C.; MS(EI,70eV): 277(M—$OH^+$,8), 276(21), 248(67), 232(45), 219(23), 161(66), 136

(59), 91(100), 89(86), 77(63); IR(KBr): 2990(OH), 1789 (C=O), 1732(C=O), 1686(C=O), 1525(NO$_2$), 1464, 1351 (NO$_2$), 1217, 949, 756 cm$^{-1}$; $^1$H-NMR(DMSO-d$_6$): 4.08(s, 2H,N—CH$_2$—CO), 4.10(s,2H,N—CH$_2$—CO), 4.73(s,2H, CH$_2$—Ar), 7.65(dd,J=7.9,7.4 Hz,1H,Ar), 7.74(d,J=7.9 Hz,1H,Ar), 8.14(s,1H,Ar), 8.16(d,J=7.4 Hz,1H,Ar), 13.09 (brs,1H,OH);

Elementary analysis (C$_{12}$H$_{11}$N$_3$O$_6$): Calculated; (C=49.15,H=3.78,N=14.33), Found (C=48.82,H=3.83,N= 14.14)

(4) Ethyl 2,4-dioxoimidazolidine-1-acetate (prepared as in paragraph (1) above) was subjected to the same reaction as in paragraph (2) above but with benzyl bromide, 4-bromobenzyl bromide, 2-bromomethyl-4-chlorobenzothiazole, 2-bromomethyl-5-chlorobenzothiazole or 2-bromomethyl-1-bromonaphtalene, respectively, to give ethyl 3-benzyl-2,4-dioxoimidazolidine-1-acetate, ethyl 3-(4-bromobenzyl)-2,4-dioxoimidazolidine-1-acetate, ethyl 3-[2-(4-chlorobenzothiazolyl)methyl]-2,4-dioximidazolidine-1-acetate, ethyl 3-[2-(5-chlorobenzothiazolyl)methyl]-2,4-dioxoimidazolidine-1-acetate or ethyl 3-[2-(1-bromonaphthyl)methyl]-2,4-dioxoimidazolidine-1-acetate, respectively. Then the same acidic hydrolysis as in paragraph (3) above was conducted to give 3-benzyl-2,4-dioxoimidazolidine-1-acetic acid [Compound 5], 3-(4-bromobenzyl)-2,4-dioxoimidazolidine-1-acetic acid [Compound 7], 3-[2-(4-chlorobenzothiazolyl) methyl]-2,4-dioxoimidazolidine-1-acetic acid [Compound 9], 3-[2-(5-chlorobenzothiazolyl)methyl]-2,4-dioxoimidazolidine-1-acetic acid [Compound 10] and 3-[2-(1-bromonaphthyl)methyl]-2,4-dioxoimidazolidine-1-acetic acid [Compound 11], respectively. The melting point, MS, IR, NMR, and elementary analysis for the compound were:

[Compound 5]

Melting point: 169.5–170.5° C.; MS(EI,70eV): 248(M$^+$, 30), 208(18), 132(15), 104(19), 91(100), 42(78); IR(KBr): 3030(OH), 1765(C=O), 1718(C=O), 1670, 1207, 1153, 957, 764, 700 cm$^{-1}$; $^1$H-NMR(DMSO-d$_6$): 4.07(s,4H,N—CH$_2$—CO), 4.57(s,2H,CH$_2$—Ar), 7.20–7.40(m,1H,Ar), 13.25(brs,1H,OH);

Elementary analysis (C$_{12}$H$_{12}$N$_2$O$_4$): Calculated; (C=58.06,H=4.87,N=11.28), Found (C=58.02,H=4.73,N= 11.32)

[Compound 7]

Melting point: 139.0–140.0° C.; MS(EI,70eV): 328(M$^+$, $^{81}$Br,18), 326(M$^+$,$^{79}$Br,20), 171(38), 169(40), 132(26), 42(100); IR(KBr): 3100(OH), 1774(C=O), 1732(C=O), 1705(C=O), 1471, 1406, 1244, 1203, 760 cm$^{-1}$; $^1$H-NMR (DMSO-d$_6$): 4.07(s,2H,N—CH$_2$—CO), 4.55(s,2H,CH$_2$—Ar), 7.23(d,J=8.3 Hz,2H,Ar), 7.53(d,J=8.3 Hz,2H,Ar), 13.00 (brs,1H,OH); Elementary analysis (C$_{12}$H$_{11}$BrN$_2$O$_4$): Calculated; (C=44.06,H=3.39,N=8.56), Found (C=43.96,H= 3.45,N=8.49)

[Compound 9]

Melting point: 114.0–115.0° C. (decomp.); MS(EI,70eV) m/z: 341(M$^+$,$^{37}$Cl,14), 339(M$^+$,$^{35}$Cl,38), 224(19), 169(24), 42(100); IR(KBr): 3283(NH), 3281(NH), 1662(C=O), 1397, 1034 cm$^{-1}$; $^1$H-NMR(DMSO-d$_6$): 4.12(s,2H,CH$_2$—CO), 4.18(s,2H,CH$_2$—CO), 5.08(s,2H,CH$_2$—Ar), 7.45(dd, J=8.2,7.6 Hz,1H,Ar—H), 7.63(dd,J=7.6,1.2 Hz,1H,Ar—H), 8.08(dd,J=8.2,1.2 Hz,1H,Ar—H);

Elementary analysis (C$_{13}$H$_{10}$ClN$_3$O$_4$S): Calculated; (C=45.96,H=2.97,N=12.37), Found (C=45.96,H=2.93,N= 12.59)

[Compound 10]

Melting point: 228.0–229.0° C.; MS(EI,70eV) m/z: 341 (M$^+$,$^{37}$Cl,17), 339(M$^+$,$^{35}$Cl,43), 224(23), 169(24), 42(100); IR(KBr): 3300(OH), 1772, 1713(C=O), 1458, 1206, 1137 cm$^{-1}$; $^1$H-NMR(DMSO-d$_6$): 4.12(s,2H,CH$_2$—CO), 4.17(s, 2H,CH$_2$—CO), 5.05(s,2H,CH$_2$—Ar), 7.51(d,J=8.2 Hz,1H, Ar—H), 8.08(s,1H,Ar—H), 8.13(d,J=8.2 Hz,1H,Ar—H), 13.05(brs,1H,COOH); Elementary analysis (C$_{13}$H$_{10}$ClN$_3$O$_4$S 2H$_2$O): Calculated; (C=45.47,H=3.05,N= 12.23), Found (C=45.70,H=3.01,N=11.86)

[Compound 11]

Melting point: 81.0–82.0° C. (decomp.); MS(EI,70eV) m/z: 378(M$^+$,$^{81}$Br,2.8), 376(M$^+$,$^{79}$Br,2.8), 297(100), 182 (25), 139(22), 42(73); IR(KBr): 3300(OH), 1766, 1714 (C=O), 1464, 1246, 761 cm$^{-1}$; $^1$H-NMR(DMSO-d$_6$): 4.12 (s,2H,CH$_2$—CO), 4.18(s,2H,CH$_2$—CO), 4.88(s,2H,CH$_2$—Ar), 7.32(d,J=8.4 Hz,1H,Ar—H), 7.63(dd,J=8.4,8.4 Hz,1H, Ar—H), 7.71(dd,J=8.4,8.4 Hz,1H,Ar—H), 7.97(d,J=8.4 Hz,1H,Ar—H), 7.99(d,J=8.4 Hz,1H,Ar—H), 8.24(d,J=8.4 Hz,1H,Ar—H), 13.07(brs,1H,COOH);

Elementary analysis (C$_{16}$H$_{13}$BrN$_2$O$_4$): Calculated; (C=50.95,H=3.47,N=7.43), Found (C=50.92,H=3.54,N= 7.44)

EXAMPLE 5

(1) A solution of 5.2 mL of diethyl azodicarboxylate in 30 mL of tetrahydrofuran was added to a solution of 5.13 g of 3-nitro-4-chlorobenzyl alcohol, 4.70 g of ethyl 2,4-dioxoimidazolidine-1-acetate and 8.68 g of triphenylphosphine in 30 mL of tetrahydrofuran at 0° C. The reaction mixture was poured over water and the mixture was extracted with ethyl acetate several times. The extracts were combined, washed with a saturated saline solution, dried over sodium sulfate and concentrated. The concentrate was purified by a silica gel column and recrystallized from a mixed solvent of ethanol and water to give 7.01 g of ethyl 3-(3-nitro-4-chlorobenzyl)-2,4-dioxoimidazolidine-1-acetate.

(2) The above-prepared dioxoimidazolidine product of paragraph (1) was hydrolyzed in the same manner as described in Example 4 paragraph (3) to give 1.42 g of 3-(3-nitro-4-chlorobenzyl)-2,4-dioxoimidazolidine-1-acetic acid [Compound 8]. The melting point, MS, IR, NMR, and elementary analysis for the compound were:

Melting point: 167.0–168.5° C.; MS(EI,70eV): 327(M$^+$, 1.6), 310(13), 195(15), 170(13), 42(100); IR(KBr): 3160 (OH), 1749(C=O), 1707(C=O), 1531(NO$_2$), 1477, 1336 (NO$_2$), 1053, 756 cm$^{-1}$; $^1$H-NMR(DMSO-d$_6$): 4.08(s,2H, N—CH$_2$—CO), 4.10(s,2H,N—CH$_2$—CO), 4.69(s,2H, CH$_2$—Ar), 7.60(d,J=8.4 Hz,1H,Ar), 7.76(d,J=8.4 Hz,1H, Ar), 7.97(s,1H,Ar), 13.08(brs,1H,OH);

Elementary analysis (C$_{12}$H$_{10}$ClN$_3$O$_6$): Calculated; (C=43.99,H=3.08,N=12.82), Found (C=43.99,H=3.22,N= 12.50)

EXAMPLE 6

(1) Ethyl isocyanatoacetate (1.9 mL) was added to a solution of 3.46 g of methyl 2-(3-nitrobenzyl)-amino-3-hydroxypropionate in 50 mL of ether at room temperature followed by vigorous stirring for seven hours. The precipitate which was separated out therefrom was collected by filtration, washed with ether and recrystallized from a mixed solvent of ethyl acetate and hexane to give 4.15 g of N-(3-nitrobenzyl)-N-[(1-methoxycarbonyl-2-hydroxy) ethyl]-N'-ethoxycarbonylmethylurea as white crystals.

(2) The above-prepared methylurea product of paragraph (1) (2.53 g) was added, at 0° C., to a solution of 0.38 g of potassium hydroxide in a mixture of ethanol and water. The mixture was stirred at room temperature for 24 hours and washed with ethyl acetate thrice. The washed mixture was acidified with concentrated hydrochloric acid and the aqueous layer was subjected to a reverse extraction with ethyl acetate. The extract was concentrated and purified by a silica gel column to give 0.10 g of 1-(3-nitrobenzyl)-5-methylidene-2,4-dioxoimidazolidine-3-acetic acid [Compound 12]. The melting point, IR, NMR, and elementary analysis for the compound were:

Melting point: 169.0–171.0° C.; IR(KBr): 3000(OH), 1738(C=O), 1718(C=O), 1662(C=O), 1527(NO$_2$), 1452, 1439, 1354(NO$_2$), 1250 cm$^{-1}$; $^1$H-NMR(DMSO-d$_6$): 4.24(s, 2H,N—CH$_2$—CO), 5.01(s,2H,CH$_2$—Ar), 5.15(d,J=2.6 Hz,1H,CH$_2$=), 5.35(d,J=2.6 Hz,1H,CH$_2$=), 7.66(dd,J=8.1, 7.7 Hz,1H,Ar), 7.75(d,J=7.7 Hz,1H,Ar), 8.17(d,J=8.1 Hz,1H,Ar), 8.20(s,1H,Ar), 13.32(brs,1H,OH);

Elementary analysis (C$_{13}$H$_{11}$N$_3$O$_6$): Calculated; (C=51.95,H=3.63,N=13.77), Found (C=50.95,H=3.61,N=13.70)

EXAMPLE 7

(1) A solution of 10 mL dimethylformamide in which 1.12 g of sodium hydride was suspended was dropped into a solution of 4.0 g of 3-(3-nitrobenzyl)-5-benzylthioxymethylimidazolidine-2,4-dione in 50 mL of dimethylformamide at not higher than 0° C. The mixture was stirred for one hour more under the same temperature condition and then dropped into a solution of 2.7 mL of ethyl bromoacetate in 40 mL of dimethylformamide at 0° C. The mixture was stirred for 2.5 hours and the reaction mixture was added to an ice-cooled 2N hydrochloric acid with vigorous stirring. Then the cooled reaction mixture was extracted with ethyl acetate several times and the combined extract was washed with a saturated physiological saline solution twice, dried over sodium sulfate and concentrated. The residue was purified by a silica gel column and recrystallized from ethanol to give 0.69 g of ethyl 3-(3-nitrobenzyl)-5-methylidene-2,4-dioxoimidazolidine-1-acetate.

(2) The above-prepared dioxoimidazolidine product of paragraph (1) (241 mg) and 50.3 mg of potassium hydroxide were suspended in a mixed solution of methanol-water followed by vigorous stirring for 24 hours. The pH of the reaction mixture was adjusted to about 4 using 2N hydrochloric acid and the reaction mixture was concentrated and extracted with ethyl acetate several times. The combined extract was dried over sodium sulfate, concentrated, washed with chloroform and the insoluble matters were filtered off. The filtrate was concentrated in vacuo to give 106 mg of 3-(3-nitrobenzyl)-5-methylidene-2,4-dioxoimidazolidine-1-acetic acid [Compound 13]. The IR and NMR for the compound were:

IR(KBr): 3000, 1781(C=O), 1714(C=O), 1664(C=O), 1527(NO$_2$), 1450, 1444, 1351(NO$_2$) cm$^{-1}$; $^1$H-NMR (DMSO-d$_6$): 4.40(s,2H,N—CH$_2$—CO), 4.84(s,2H,CH$_2$—Ar), 5.17(d,J=1.9 Hz,1H,CH$_2$=), 5.36(d,J=1.9 Hz,1H, CH$_2$=), 7.66(dd,J=7.6,7.6 Hz,1H,Ar), 7.73(d,J=7.6 Hz,1H, Ar), 8.14(s,1H,Ar), 8.16(d,J=7.6 Hz,1H,Ar)

EXAMPLE 8

(1) N-(3-Nitrobenzyl)urea (78 g) was dissolved in 500 mL of 80% acetic acid, 120 g of benzyl 2-benzyloxy-2-hydroxyacetate was added thereto at 80° C. and the mixture was stirred at 80° C. for two hours. The mixture was concentrated in vacuo and the solvent was evaporated therefrom by means of an azeotropic distillation with toluene. The residue was purified by a silica gel column and recrystallized from a mixed solvent of ethyl acetate and hexane to give 49 g of 5-hydroxy-1-(3-nitrobenzyl)-2,4-dioxoimidazolidine.

(2) The above-prepared dioxoimidazolidine product of paragraph (1) (12.5 g) and 10 g of potassium bicarbonate were suspended in 150 mL of acetone, 9 mL of tert-butyl bromoacetate was added thereto and the mixture was heated to reflux for eight hours with stirring. Insoluble matters were filtered off, the filtrate was concentrated in vacuo, the residue was dissolved in ethyl acetate and the solution was washed with water and a saturated saline solution. Then the solution was dried over sodium sulfate, ethyl acetate was evaporated therefrom and the resulting residue was purified by a silica gel column to give 12.4 g of tert-butyl 5-hydroxy-1-(3-nitrobenzyl)-2,4-dioxoimidazolidine-3-acetate.

(3) The above-prepared dioxoimidazolidine-3-acetate product of paragraph (2) (3.6 g) was dissolved in a mixed solvent of 4N hydrochloric acid and dioxane and the solution was stirred at room temperature for six hours. The reaction solution was concentrated in vacuo to dryness and then chloroform was added to the residue. The crystals were dislodged from the wall of the reaction flask with a spatula. The solid was collected by filtration, washed with chloroform and dried to give 0.8 g of 5-hydroxy-1-(3-nitrobenzyl)-2,4-dioxoimidazolidine-3-acetic acid [Compound 14] as amorphous crystals. The melting point, MS, IR, NMR, and elementary analysis for the compound were:

Melting point: 123.0–125.0° C.; MS(SIMS,glycerol) m/z: 310[M+H]$^+$; IR(KBr): 1782, 1718, 1529, 1466, 1352, 1236 cm$^{-1}$; $^1$H-NMR(DMSO-d$_6$): 4.09(d,J=17.6 Hz,2H,CH$_2$—CO$_2$), 4.13(d,J=17.6 Hz,2H,CH$_2$—CO$_2$), 4.58(d,J=16.2 Hz,2H,CH$_2$—Ar), 4.68(d,J=16.2 Hz,2H,CH$_2$—Ar), 5.28(s, 1H,CH), 7.36(brs,1H,OH), 7.65(dd,J=8.1,7.7 Hz,1H,Ar—H-5), 7.79(d,J=7.7 Hz,1H,Ar—H-6), 8.14(d,J=8.1 Hz,1H, Ar—H-4), 8.20(s,1H,Ar—H-2), 13.13 (brs, 1H,COOH);

Elementary analysis (C$_{12}$H$_{11}$N$_3$O$_7$): Calculated; (C=46.61,H=3.58,N=13.59), Found (C=46.35,H=3.60,N=13.72)

EXAMPLE 9

(1) Ethyl N-carbamoylaminoacetate was made to react with benzyl 2-benzyloxy-2-hydroxyacetate in the same manner as mentioned in Example 8 paragraph (1) to give ethyl 5-hydroxy-2,4-dioxoimidazolidine-1-acetate.

(2) The above-prepared dioxoimidazolidine-1-acetate product of paragraph (1) was condensed with 3-nitrobenzyl bromide in the same manner as mentioned in Example 8 paragraph (2) to give ethyl 5-hydroxy-3-(3-nitrobenzyl)-2,4-dioxoimidazolidine-1-acetate.

(3) The above-prepared dioxoimidazolidine-1-acetate product of paragraph (2) (15 g) was suspended in a mixed solvent of acetic acid and hydrochloric acid and the mixture was heated to reflux with stirring for two hours. Then the mixture was concentrated in vacuo, ether-chloroform was added thereto. The crystals were dislodged from the wall of the reaction flask with a spatula. The solid was washed with ether and recrystallized from a mixed solvent of ethanol and water to give 8.1 g of 5-hydroxy-3-(3-nitrobenzyl)-2,4-dioxoimidazolidine-1-acetic acid [Compound 15]. The melting point, MS, IR, NMR, and elementary analysis for the compound were:

Melting point: 153.0–155.0° C.; MS(SIMS,glycerol) m/z: 310[M+H]$^+$; IR(KBr): 3533, 3494, 3431, 1776, 1735, 1713, 1527, 1468, 1350, 1238 cm$^{-1}$; $^1$H-NMR(DMSO-d$_6$): 3.90 (d,J=18.0 Hz,2H,CH$_2$—CO$_2$), 4.16(d,J=18.0 Hz,2H,CH$_2$—CO$_2$), 4.73(d,J=15.6 Hz,2H,CH$_2$—Ar), 4.78(d,J=15.6

Hz,2H,CH$_2$—Ar), 5.24(s,1H,CH), 7.20(brs,1H,OH), 7.66 (ddd,J=8.0,7.6,1.0 Hz,1H,Ar—H-5), 7.76(d,J=7.6 Hz,1H, Ar—H-6), 8.15–8.17(m,2H,Ar—H-2,Ar—H-4), 13.00(brs, 1H,COOH);

Elementary analysis (C$_{12}$H$_{11}$N$_3$O$_7$): Calculated; (C=46.61,H=3.58,N=13.59), Found (C=46.88,H=3.72,N= 13.81)

EXAMPLE 10

(1) A dimethyl sulfoxide solution (150 mL) containing 10.02 g of uracil, 3.3 mL of ethyl bromoacetate, 13.85 g of potassium carbonate and 4.52 g of sodium iodide was stirred at 90° C. for six hours. The reaction mixture was poured over water and the mixture was extracted with chloroform. The extracts were combined, dried over sodium sulfate and concentrated in vacuo. The concentrate was poured over a saturated saline solution, the mixture was extracted with ethyl acetate and the extract was dried over sodium sulfate. After concentration, the resulting residue was recrystallized from ethyl acetate to give 2.30 g of ethyl 2,4-dioxo-1,2,3, 4-tetrahydropyrimidine-1-acetate.

(2) The above-prepared pyrimidine-1-acetate product of paragraph (1) was dissolved in 40 mL of dimethyl sulfoxide and the solution was dropped into a suspension of 0.58 g of sodium hydride in 30 mL of dimethylformamide at not higher than 0° C. The mixture was stirred for 1.5 hours more and a solution of 3.42 g of 3-nitrobenzylbromide in 70 mL of dimethylformamide was added thereto at 0° C. The reaction mixture was stirred at 0° C. for two hours, poured over water and the mixture was extracted with ethyl acetate several times. The extracts were combined, washed with saturated saline solution, dried and concentrated. Then it was purified by a silica gel column and recrystallized from ethanol to give 1.86 g of ethyl 3-(3-nitrobenzyl)-2,4-dioxo-1,2,3,4-tetrahydropyrimidine-1-acetate.

(3) The above-prepared pyrimidine-1-acetate product of paragraph (2) (1.60 g), 6 mL of acetic acid and 2 mL of hydrochloric acid were mixed followed by heating to reflux for two hours. After concentration, it was heated to reflux for two hours more with 6 mL of acetic acid and 2 mL of hydrochloric acid. The solvent was evaporated therefrom and the residue was washed with water and recrystallized from ethanol to give 1.39 g of 3-(3-nitrobenzyl)-2,4-dioxo-1,2,3,4-tetrahydropyrimidine-1-acetic acid [Compound 16] as white crystals. The melting point, MS, IR, NMR, and elementary analysis for the compound were:

Melting point: 161.0–161.5° C.; MS(EI,70eV): 305(M$^+$, 47), 288(40), 161(48), 128(19), 82(100); IR(KBr): 2980 (OH), 1734(C=O), 1703(C=O), 1637, 1601, 1537(NO$_2$), 1470, 1350(NO$_2$), 1238, 1200 cm$^{-1}$; $^1$H-NMR(DMSO-d$_6$): 4.50(s,2H,N—CH$_2$—CO), 5.10(s,2H,CH$_2$—Ar), 5.83(d,J= 7.9 Hz,1H,COCH=C), 7.62(dd,J=7.9,7.9 Hz,1H,Ar), 7.72 (d,J=7.7 Hz,1H,Ar), 7.73(d,J=7.9 Hz,1H,COC=CH), 8.12 (s,1H,Ar), 8.13(d,J=7.9 Hz,1H,Ar), 13.20(brs,1H,OH);

Elementary analysis (C$_{13}$H$_{11}$N$_3$O$_6$): Calculated; (C=51.15,H=3.63,N=13.77), Found (C=50.95,H=3.83,N= 13.76)

(4) Similarly prepared as in paragraphs (1) and (2) above were: ethyl 3-(3-chloro-4-nitrobenzyl)-2,4-dioxo-1,2,3,4-tetrahydropyrimidine-1-acetate, ethyl 3-[2-(4-chlorobenzothiazolyl)methyl]-2,4-dioxo-1,2,3,4-tetrahydropyrimidine-1-acetate, ethyl 3-[2-(5-chlorobenzothiazolyl)methyl]-2,4-dioxo-1,2,3,4-tetrahydropyrimidine-1-acetate or ethyl 3-[2-(1-bromonaphtyl)methyl]-2,4-dioxo-1,2,3,4-tetrahydropyrimidine-1-acetate. Each of the compounds was then subjected to an acidic hydrolysis to give, respectively, 3-(3-chloro-4-nitrobenzyl)-2,4-dioxo-1,2,3,4-tetrahydropyrimidine-1-acetic acid [Compound 17], 3-[2-(4-chlorobenzothiazolyl)methyl]-2,4-dioxo-1,2,3,4-tetrahydropyrimidine-1-acetic acid [Compound 18], 3-[2-(5-chlorobenzothiazolyl)methyl]-2,4-dioxo-1,2,3,4-tetrahydropyrimidine-1-acetic acid [Compound 19] and 3-[2-(1-bromonaphtyl)methyl]-2,4-dioxo-1,2,3,4-tetrahydro-pyrimidine-1-acetic acid [Compound 20] as white crystals. The melting point, MS, IR, NMR, and elementary analysis for the compounds were:

[Compound 17]

Melting point: 184.0–185.0° C.; MS(EI,70eV) m/z: 341 (M$^+$,$^{37}$Cl,8.7), 339(M$^+$,$^{35}$Cl,26), 324(14), 332(38), 195(43), 82(100); IR(KBr): 1735(C=O), 1706(C=O), 1662, 1658, 1553(NO$_2$), 1461, 1349(NO$_2$), 770 cm$^{-1}$; $^1$H-NMR(DMSO-d$_6$): 4.48(s,2H,N—CH$_2$—CO$_2$), 5.05(s,2H,CH$_2$—Ar), 5.82 (d,J=8.0 Hz,1H,CH=), 7.57(dd,J=8.2,1.6 Hz,1H,Ar—H), 7.73(d,J=8.2 Hz,1H,Ar—H), 7.74(d,J=8.0 Hz,1H,CH=), 7.93(d,J=1.6 Hz,1H,Ar—H), 13.20(brs,1H,COOH);

Elementary analysis (C$_{13}$H$_{10}$ClN$_3$O$_6$): Calculated; (C=45.97,H=2.97,N=12.37), Found (C=46.17,H=2.82,N= 12.43)

[Compound 18]

Melting point: 184.0–185.0° C. (decomp.); MS(EI,70eV) m/z: 353(M$^+$,$^{37}$Cl,27), 351(M$^+$,$^{35}$Cl,73), 224(73), 196(23), 169(78), 128(69), 82(100); IR(KBr): 3300(OH), 1729, 1705 (C=O), 1661(C=O), 1447, 1107 cm$^{-1}$; $^1$H-NMR(DMSO-d$_6$): 4.53(s,2H,N—CH$_2$—CO$_2$), 5.43(s,2H,CH$_2$—Ar), 5.92 (d,J=8.0 Hz,1H,CH=), 7.45(dd,J=7.8,7.6 Hz,1H,Ar—H), 7.62(d,J=7.8 Hz,1H,Ar—H), 7.81(d,J=8.0 Hz,1H,CH=), 8.05(d,J=7.6 Hz,1H,Ar—H), 13.20(brs,1H,COOH); Elementary analysis (C$_{14}$H$_{10}$ClN$_3$O$_4$S): Calculated; (C=47.80,H=2.86,N=11.95), Found (C=48.21,H=2.79,N= 11.88)

[Compound 19]

Melting point: 208.0–209.0° C.; MS(EI,70eV) m/z: 353 (M$^+$,$^{37}$Cl,34), 351(M$^+$,$^{35}$Cl,75), 224(91), 196(30), 169(100), 128(57), 82(98); IR(KBr): 1716(C=O), 1685(C=O), 1453, 1362 cm$^{-1}$; $^1$H-NMR(DMSO-d$_6$): 4.53(s,2H,N—CH$_2$—CO$_2$), 5.41(s,2H,CH$_2$—Ar), 5.88(d,J=7.8 Hz,1H,CH=), 7.49(dd,J=8.6,2.0 Hz,1H,Ar—H), 7.79(d,J=7.8 Hz,1H, CH=), 8.05(d,J=2.0 Hz,1H,Ar—H), 8.10(d,J=8.6 Hz,1H, Ar—H);

Elementary analysis (C$_{14}$H$_{10}$ClN$_3$O$_4$S): Calculated; (C=47.80,H=2.86,N=11.95), Found (C=47.94,H=3.01,N= 11.83)

[Compound 20]

Melting point: 208.0–209.0° C.; MS(EI,70eV) m/z: 309 ($^+$-Br,100), 219(10), 182(55); IR(KBr): 3452(OH), 1739, 1705(C=O), 1658(C=O), 1455, 1199 cm$^{-1}$; $^1$H-NMR (DMSO-d$_6$): 4.53(s,2H,N—CH$_2$—CO$_2$), 5.24(s,2H,CH$_2$—Ar), 5.90(d,J=7.8 Hz,1H,CH=), 7.00(d,J=7.8 Hz,1H,Ar—H), 7.61(dd,J=8.6,8.6 Hz,1H,Ar—H), 7.71(dd,J=8.4,8.4 Hz,1H,Ar—H), 7.84(d,J=7.8 Hz,1H,CH—), 7.91(d,J=8.4 Hz,1H,Ar—H), 7.97(d,J=7.8 Hz,1H,Ar—H), 8.24(d,J=8.4 Hz,1H,Ar—H), 13.25(brs,1H,COOH);

Elementary analysis (C$_{17}$H$_{13}$BrN$_2$O$_4$ 1EtOH): Calculated; (C=52.46,H=3.48,N=7.11), Found (C=52.75,H=3.84, N=6.77)

EXAMPLE 11

(1) A solution of 100 mL of hexamethyldisilazane containing 5.29 g of uracil and 12.0 mL of chlorotrimethylsilane was heated to reflux for two hours. The transparent reaction solution was concentrated in vacuo, a solution of 14.0 g of 3-nitrobenzyl bromide and 1.11 g of tetrabutylammonium iodide in 100 mL of methylene chloride was added thereto and the mixture was stirred at room temperature for four days. The reaction solution was poured over water and the crystals separated out therefrom were collected by filtration, washed with water and ethyl acetate and dried to give 8.60 g of 3-(3-nitrobenzyl)uracil.

(2) The above-prepared uracil product of paragraph (1) (5.91 g) was dissolved in 100 mL of dimethyl sulfoxide, the solution was added to a suspension of 1.21 g of sodium hydride in 20 mL of dimethyl sulfoxide at 0° C. and the mixture was stirred for three hours. A solution of 2.7 mg of ethyl bromoacetate in 20 mL dimethyl sulfoxide was dropped into the reaction mixture, stirred for 2.5 hours and poured over water. The product was purified by a silica gel column and recrystallized from ethanol to give 3.15 g of ethyl 1-(3-nitro-benzyl)-2,4-dioxo-1,2,3,4-tetrahydropyrimidine-3-acetate.

(3) The above-prepared pyrimidine-3-acetate product of paragraph (2) (2.29 g) was subjected to an acidic hydrolysis in the same manner as mentioned in Example 8 paragraph 3 to give 1.82 g of 1-(3-nitrobenzyl)-2,4-dioxo-1,2,3,4-tetrahydropyrimidine-3-acetic acid [Compound 21]. The melting point, MS, IR, and NMR analyses for the compound were:

Melting point: 200.0–201.5° C.; MS(EI,70eV): 305($M^+$, 47), 287(26), 203(74), 187(70), 136(94), 90(100); IR(KBr): 2900(OH), 1741(C=O), 1705(C=O), 1637, 1608, 1524 ($NO_2$), 1463, 1350($NO_2$), 920, 771 $cm^{-1}$; $^1$H-NMR(DMSO-$d_6$): 4.46(s,2H,N—$CH_2$—CO), 5.10(s,2H,$CH_2$—Ar), 5.86 (d,J=7.9 Hz,1H,COCH=C), 7.68(dd,J=8.5,7.5 Hz,1H,Ar), 7.78(d,J=7.7 Hz,1H,Ar), 8.00(d,J=7.9 Hz,1H,COC=CH), 8.18(d,J=8.1 Hz,1H,Ar), 8.22(s,1H,Ar), 12.99(brs,1H,OH)

EXAMPLE 12

Compounds of the present invention were evaluated for pharmaceutical action and selectivity by measuring the rate of inhibition towards an aldose reductase and towards an aldehyde reductase:

(1) Inhibitory Action Towards Aldose Reductase

Action of the compounds of the present invention for inhibiting an aldose reductase was investigated using the aldose reductase which was prepared from lenses of rats. Thus, a compound was added to a reaction system comprising a phosphate buffer, NADPH (β-nicotinamide adenine dinucleotide phosphate, reduced form) and aldose reductase. After confirming for several minutes that the absorbencies became stable, glyceraldehyde was added thereto and a decrease in the absorbance at 340 nm with a lapse of time was measured whereby the inhibitory action of the compound to the aldose reductase was determined.

Examples of the results are given in Table 1 in which the inhibiting rate to the aldose reductase is the value when the concentration of the compound was $1 \times 10^{-7}$M:

TABLE 1

| Compound No. | Inhibiting rate | Compound No. | Inhibiting rate |
|---|---|---|---|
| Compound 2 | 70% | Compound 15 | 45% |
| Compound 6 | 38% | Compound 16 | 77% |
| Compound 8 | 84% | Compound 17 | 58% |
| Compound 9 | 56% | Compound 18 | 64% |
| Compound 10 | 48% | Compound 19 | 80% |
| Compound 12 | 75% | Compound 20 | 31% |
| Compound 13 | 99% | | |

It is clear from the above-mentioned results of the pharmacological tests, that the carboxyalkyl heterocyclic derivatives of the present invention exhibit an excellent inhibitory action towards aldose reductase with a low toxicity whereby they are very useful as therapeutic agents for diabetic complications. Thus, they are useful as drugs for therapy and prevention of various types of diabetic complications caused by an excessive accumulation of intracellular sorbitol such as diabetic neuropathy, diabetic cataract and retinopathy, diabetic nephropathy, diabetic dermopathy and other diabetic microangiopathy.

2. Inhibitory Action Towards Aldehyde Reductase

The inhibitory action of the compounds of the present invention to an aldehyde reductase obtained from rat kidney was measured using the compounds at a concentration of $1 \times 10^{-4}$M but the inhibition was hardly noted. Thus, the compounds of the present invention having a high enzyme selectivity to aldose reductase participating in the production of sorbitol which induces diabetic complications exhibit low toxicity and high safety. Therefore, they are particularly useful for the therapy of the above-mentioned chronic diseases which require administration of a drug for a prolonged period.

The compounds of the present invention can be made into pharmaceutical preparations by combining one or more of the compounds with at least one pharmaceutical carrier or diluent. They can be made into various types of preparations by known methods. The compounds of the invention can be made into solid, semisolid, liquid or aerosol formulations for administration by oral or parenteral means.

The compounds of the present invention may be used either solely or jointly in pharmaceutically effective amounts for treating animals or humans. They may also be used in pharmaceutically effective amounts in combination with pharmaceutically effective amounts of other pharmaceutically active components in pharmaceutical compositions or preparations.

In the case of preparations for oral administration, one or more of the compounds of the present invention alone or together with commonly-used pharmaceutically acceptable excipients in pharmaceutically acceptable amounts such as a suitable pharmaceutically acceptable additive or carrier (e.g. lactose, mannitol, corn starch, potato starch, etc.) may be mixed with one or more pharmaceutically acceptable: (1) binders such as crystalline cellulose, cellulose derivatives, gum arabicum, corn starch, gelatin, etc., (2) disintegrating agents such as corn starch, potato starch, potassium carboxymethylcellulose, etc., (3) lubricating agents such as talc, magnesium stearate, etc., and (4) other pharmaceutically acceptable excipients including pharmaceutically acceptable bulking agents, moisturizing agents, buffers, preservatives, perfumes and the like to obtain tablets, diluted powders, granules or capsules.

Alternatively, suppositories may be prepared by mixing at least one compound of the present invention with pharmaceutically acceptable amounts of one or more pharmaceutically acceptable fatty/oily bases (e.g. cacao butter), emulsified bases, water-soluble bases (e.g. Macrogol), hydrophilic bases, etc.

In the case of parenteral administration using injections, for example, it is possible to prepare solutions or suspensions of one or more compounds of the present invention in pharmaceutically acceptable carriers such as aqueous and nonaqueous solvents such as distilled water for injection, physiological saline solution, Ringer's solution, plant oil, synthetic fatty acid glycerides, higher fatty acid esters, propylene glycol, etc.

In the case of inhalations or aerosol preparations, at least one compound of the present invention in the form of a liquid or minute powder can be filled up in an aerosol container with a gas or liquid spraying agent, and if desired, with conventional adjuvants such as one or more pharmaceutically acceptable humidifying agents or dispersing agents. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiologically saline solution, or a non-aqueous solvent for injection. The collyriums may also include pharmaceutically acceptable preservants, sterilizing agents, pH adjusting agents, and the like.

It is also possible, depending upon the type of the disease, to prepare pharmaceutical preparations other than the above-mentioned ones such as ointments, poultices, etc. which are most suitable for therapy depending upon the state of the patient and the type of disease.

The preferred dosage of the compound of the present invention varies depending upon the subject to be administered (age, body weight, symptoms, etc. of the patient), form of the preparation, method for the administration, treatment for the administration, etc. To achieve the desired result, the compound may be usually administered by the oral route with a daily dose of 10–3,000 mg, preferably 20–1,500 mg per day, to common adults.

In the case of parenteral administration such as by injection, the preferred dosage may be from one-third to one-tenth of the above-mentioned oral dosage because of the effects of absorption, etc. in the oral route.

We claim:

1. A compound represented by the general formula (I) or a pharmaceutically acceptable salt thereof:

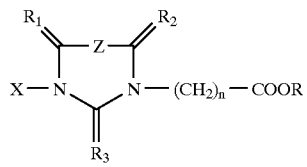

(I)

wherein two of the substituents $R_1$, $R_2$ and $R_3$ are oxygen while the remaining substituent is methylidene, two hydrogen atoms, or a hydrogen atom and a hydroxyl group;

X is
  benzyl substituted with one nitro and/or substituted with one halogen,
  benzothiazolylmethyl which may be substituted with nitro and/or substituted with halogen, or
  naphthylmethyl which may be substituted with nitro and/or substituted with halogen;

R is hydrogen or lower alkyl; and n is an integer of 1 to 3.

2. A compound represented by the general formula (II) or a pharmaceutically acceptable salt thereof:

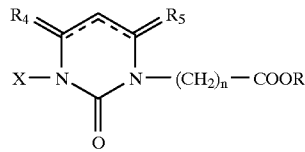

(II)

wherein one of $R_4$ and $R_5$ is oxygen while the other is two hydrogen atoms;

X is
  benzyl substituted with one nitro and/or substituted with one halogen,
  benzothiazolylmethyl which may be substituted with nitro and/or substituted with halogen, or
naphthylmethyl which may be substituted with nitro and/or substituted with halogen;

R is hydrogen or lower alkyl;

n is 1 to 3; and the two broken lines in the general formula (II) represent one single bond and one double bond with the single bond being on the same side as the oxygen substituent represented by $R_4$ or $R_5$.

3. A compound according to claim 1 wherein X is a 3-nitrobenzyl group.

4. A compound according to claim 1 wherein $R_1$ and $R_2$ are each oxygen.

5. A compound according to claim 1 wherein $R_2$ and $R_3$ are each oxygen.

6. A compound according to claim 1 wherein $R_1$ and $R_3$ are each oxygen.

7. A compound according to claim 6 wherein $R_2$ is two hydrogens each bonded to the ring.

8. A compound according to claim 6 wherein $R_2$ is methylidene.

9. A compound according to claim 6 wherein $R_2$ is hydrogen and hydroxyl each bonded to the ring.

10. A compound according to claim 2 wherein $R_4$ is oxygen.

11. A pharmaceutical composition for the treatment of diabetic complications comprising at least one of the compounds of claim 1 in a pharmaceutically effective amount and a pharmaceutically acceptable carrier.

12. A pharmaceutical composition for the treatment of diabetic complications comprising at least one of the compounds of claim 2 in a pharmaceutically effective amount and a pharmaceutically acceptable carrier.

13. A pharmaceutical composition as claimed in claim 11 wherein at least one of said compounds is a pharmaceutically acceptable salt.

14. A pharmaceutical composition as claimed in claim 12 wherein at least one of said compounds is a pharmaceutically acceptable salt.

15. A method for the treatment of diabetic complications caused by excessive accumulation of intracellular sorbitol comprising administering a pharmaceutically effective amount of at least one compound according to claim 1 to substantially inhibit aldose reductase without substantially inhibiting aldehyde reductase.

16. A compound according to claim 2 wherein X is a 3-nitrobenzyl group.

17. A method for the treatment of diabetic complications caused by excessive accumulation of intracellular sorbitol comprising administering a pharmaceutically effective amount of at least one compound according to claim 2 to substantially inhibit aldose reductase without substantially inhibiting aldehyde reductase.

* * * * *

UNITED STATES PATENT AND TRADEMARK OFFICE
CERTIFICATE OF CORRECTION

PATENT NO. : 5,912,261
DATED      : June 15, 1999
INVENTOR(S) : Kotani et al.

It is certified that error appears in the above-identified patent and that said Letters Patent is hereby corrected as shown below:

Title page, under item [56], at the end of "Other Publications"

please insert:

"Pathologic Biochemistry and Clinics of Free Radicals,

Inflammation and Antiinflammation," Nippon Rinsho, vol. 46, no. 10, pps. 93-97 (1988)

Yonezawa et al., Nippon Kagaku Zasshi, 89, no. 8, pps. 62-64

(1968)

Signed and Sealed this

Sixth Day of February, 2001

Attest:

Q. TODD DICKINSON

*Attesting Officer*    *Director of Patents and Trademarks*